(12) United States Patent
Su

(10) Patent No.: US 6,332,360 B1
(45) Date of Patent: Dec. 25, 2001

(54) APPARATUS FOR MEASURING THE DEPTH, WATER VELOCITY OR WATER TEMPERATURE OF AN OPEN CHANNEL

(75) Inventor: Tyan Khak Su, Sungnam (KR)

(73) Assignee: Toho Keisoku Institute, Tokyo (JP)

( * ) Notice: Subject to any disclaimer, the term of this patent is extended or adjusted under 35 U.S.C. 154(b) by 0 days.

(21) Appl. No.: 09/391,229

(22) Filed: Sep. 7, 1999

(30) Foreign Application Priority Data

Sep. 16, 1998 (JP) .................................................. 10-279306

(51) Int. Cl.⁷ ............................ G01N 29/18; G01F 13/00
(52) U.S. Cl. ..................... 73/597; 73/861.25; 73/861.27
(58) Field of Search ................... 73/597, 170.13, 73/170.33, 170.34, 861.25, 861.26, 861.27, 861.28, 290 V

(56) References Cited

U.S. PATENT DOCUMENTS

| | | | |
|---|---|---|---|
| 4,480,466 | * 11/1984 | Gates ...................................... | 73/195 |
| 5,515,721 | 5/1996 | Kim et al. ........................... | 73/170.13 |
| 5,531,124 | 7/1996 | Kim et al. ........................... | 73/861.27 |
| 5,531,125 | 7/1996 | Ahn et al. ........................... | 73/861.27 |
| 5,734,111 | 3/1998 | Hak Soo ............................. | 73/861.25 |
| 5,780,747 | 7/1998 | Soo .................................... | 73/861.29 |
| 6,089,104 | * 7/2000 | Chang ................................ | 73/861.27 |

FOREIGN PATENT DOCUMENTS

| | | |
|---|---|---|
| A 9-196727 | 7/1997 | (JP) . |
| B1 2863748 | 12/1998 | (JP) . |

\* cited by examiner

Primary Examiner—Hezron Williams
Assistant Examiner—Jacques Saint-Surin
(74) Attorney, Agent, or Firm—Oliff & Berridge PLC

(57) ABSTRACT

An apparatus for measuring the depth of water and the water temperature at any point of an open channel by measuring an ultrasonic propagation time transmitted between a plural number of ultrasonic transducers and by a calculation using an ultrasonic velocity, wherein a slider 11 is attached to a support 13 capable of moving up and down, which is placed in water. A first ultrasonic transducer 18 is fixed to the bottom of the support 13 and a second ultrasonic transducer 19 is positioned above the first ultrasonic transducer 18. A third ultrasonic transducer 21 is positioned above the second ultrasonic transducer 19 and below the slider 11 and a fourth ultrasonic transducer 22 is fixed to the slider 11. Each transducer faces with each other. The apparatus further comprises a fifth transducer 23 and a sixth transducer 24 for measuring the flow velocity, both of which transmit and receive ultrasonic waves.

13 Claims, 5 Drawing Sheets

APPARATUS FOR MEASURING THE DEPTH, WATER VELOCITY OR WATER TEMPERATURE OF AN OPEN CHANNEL

BACKGROUND OF THE INVENTION

The invention relates to an apparatus for measuring the vertical average flow velocity and the depth of water to measure the flow quantity of an open channel, e.g., a river. The invention also relates to a measuring apparatus for measuring the depth of water, water velocity and water temperature of a lake, dam, reservoir, river and the like.

As a typical method for measuring the flow quantity of a point of an open channel such as river, it is know that a cross section of the point and the flow quantity of the point are to be measured. It's specific method is as follows. First, an open channel is divided into a number of sections along a imaginary line drawn along the width of the channel. Then, in each section, the flow velocities are measured at various vertical depths along the vertical center line thereof using a propeller flow-meter, e.g. Based on this, the average flow quantity of each section is calculated. Then, the flow quantity of each point is calculated by multiplying the average flow velocity by the cross section. Finally, the open channel's flow quantity is obtained by summing the all flow quantities of the points.

This conventional method is disclosed in Japanese patent provisional publication No. 9-196727, entitled "Apparatus and method for measuring the river flow quantity", and Japanese patent application No. 9-340875, entitled "Apparatus for measuring the flow velocity" which is not published yet.

The accuracy in the conventional method for measuring the flow quantity becomes higher when many vertical lines are provided to divide the cross section of the water. The vertical lines should be prepared at least 10. In order to measure the average vertical flow velocity along a vertical line, a local flow velocity should be measured at various depths utilizing a local flow velocity gauge (for instance, a propeller-type gauge). The average vertical flow velocity is calculated by substituting the values obtained by the measurement into a formula. When an accuracy in a measurement is required, each vertical line should be divided into 5 to 10, and the local flow velocity is to be measured at each point.

However, since the flow velocity roughly varies at each local point, it takes more than 60 seconds in a measurement operation in each point. When there are provided 10 vertical lines, and the flow velocity is measured at 5 points on each vertical line, it requires more than 3000 seconds to complete the measurement operation. Further, considering the time period needed for moving a measuring apparatus or a gauge, a lot of time is required for a measurement of the flow quantity. Besides, a lot of manpower is needed.

To ease the heavy work needed in the conventional method, there is a permanent river flow quantity measurement post, which automatically measures the local flow velocities along the vertical lines by moving a local flow measuring gauge with, for example, a carrier. However, this method also requires a lot of time to complete the measurement. This problem remain unchanged. Further, in case the flow quantity varies shortly, the obtained flow quantity which has been measured a while ago differ from the flow quantity flowing right now.

In order to solve such drawback, there is a consideration of reducing a number in the local flow velocity measuring points or reducing a time period used in measuring the flow velocity at each local point. However, in doing so, the errors in the local flow quantity and the flow variation are generated. Subsequently, the error in the flow quantity measurement becomes larger.

In order to solve the drawback in the conventional method, a new apparatus for measuring the flow velocity has been developed. The apparatus basis a principle that the propagation velocity of an ultrasonic wave and the frequency of the reflected wave vary in water depending on the flow velocity. This type of apparatus for measuring the flow velocity is superior to the aforementioned mechanical-type measuring method which has commonly been used. That is, it does not disturb the flow velocity of an open channel; it is stable in measurement through the dead flow velocity to the high flow velocity, so that a line showing the measured velocities in a graph is linear; it can measure the directional element of the flow velocity; it can be used in real time measurement; it performs continuous automatic measurement; it is easily maintained since it includes no parts which are mechanically operated.

The method for measuring the flow velocity using the ultrasonic wave includes a propagation time difference method, a phase difference method, a sing around method, Doppler effect method and a beam displacement method. Among these methods, an apparatus using the propagation time difference method is disclosed in the aforementioned Japanese patent provisional publication No. 9-196727 and Japanese patent application No. 9-340875. The apparatus measures the vertical average flow velocity from the water bed to the water surface of an open channel by use of the ultrasonic wave.

The method for measuring the flow velocity utilizing the propagation time difference will be described below referring to an apparatus disclosed in Japanese provisional publication No. 9-196727. As illustrated in FIG. 5, a pair of transducers 1, 1' for measuring the flow velocity is positioned just below the water surface as it is fixed to a catamaran float 4 which is floating on the water surface. Each transducer is positioned at an equal distance D from the center of the float 4 in the same level. A transducer 2 for measuring the water depth is positioned just below the water surface along the center of the catamaran float 4. Another transducer 2' for measuring the water depth is positioned below the transducer 2 with a vertical distance l. Further, an ultrasonic reflecting device 3 is positioned on the river bed as needed.

In FIG. 5, the distance L is a space between the transducer 2 for measuring the water depth and the upper surface of the ultrasonic reflecting device 3. When a distance between the surface of the river and the transducer 2 is a, the water depth H=L+(a+b). The vertical distance l is arranged to a length which is less than ½ of the water depth H.

The propagation time periods $t_2$ and $t_{2'}$ are calculated by the equations (a) as shown below. The propagation time period $t_2$ is a time period between the time an ultrasonic wave is transmitted from the transducer 2 and the time it returns to the transducer 2 after reflecting at the reflecting device 3. The propagation time period $t_{2'}$ is a time period between the time an ultrasonic wave is transmitted from the transducer 2' and the time it returns to the transducer 2' after reflecting at the reflecting device 3.

$$t_2 = \frac{2L}{c_2}, \quad t'_2 = \frac{2(L-l)}{c'_2} \quad (a)$$

In explaining the same point of the prior art disclosed in Japanese provisional publication No. 9-196727 in a different expression, when the ultrasonic velocity measured at a point on the vertical distance l is Cl, the ultrasonic velocity Cl is obtained by equation (b). And, when the total average ultrasonic velocity in the distance L is CL, the distance L is obtained by equation (c). Therefore, supposing the distance L is a distance L', the distance L is obtained by equation (d) which is formulated by substituting the equation (c) into the equation (b). (The rightmost side formula in the equation (d) is the same expression as that described in the above-mentioned prior invention.)

$$c_l = \frac{2l}{t_2 - t'_2} \quad (b)$$

$$L = \frac{c_L \cdot t_2}{2} \quad (c)$$

$$L' = \frac{t_2}{2} c_l = \frac{t_2}{t_2 - t'_2} l \quad (d)$$

Further, the time difference Δt is measured, which is a time difference between a first time period and a second time period. The first time period is a time in that an ultrasonic wave is transmitted from the transducer 1 and is received by the transducer 1' after reflecting at the reflecting device 3. The second time period is a time in that an ultrasonic wave is transmitted from the transducer 1' and is received by the transducer 1 after reflecting at the reflecting device 3.

A general formula for calculating the vertical average flow velocity is shown in equation (e). In this equation, C is the average ultrasonic velocity of the instant velocities transmitted in the ultrasonic propagation route, so that CL should be used as C. However, supposing the vertical average flow velocity is $V_\perp$, when Cl=CL, the vertical average flow velocity $V^\perp$ between the river bed (or near the river bed) and the river surface (or near the river surface) is calculated by equation (f), which is formulated by substituting the equation (b) into the equation (e). Numeral reference "⊥" in the vertical average velocity $V_\perp$ denotes the "vertical" of the vertical average velocity. Reference numeral D is a direct distance between the transducers 1 and 1'. The rightmost side of the equation (f) is similar to the equation disclosed in the aforementioned prior invention.

$$V_\perp = \frac{\Delta t}{2D} c^2 \quad (e)$$

$$V'_\perp = \frac{\Delta t}{2D} c_l^2 = \frac{\Delta t}{2D} \left( \frac{2l}{t_2 - t'_2} \right)^2 \quad (f)$$

However, when the water depth and the flow velocity are measured in accordance with the prior art, errors in measurement become significant. That is, in the prior art, as clearly shown in the equations (d) and (f), the length and the flow velocity of the distance L are obtained based on the local ultrasonic velocity cl measured along the vertical distance l, and they are not obtained based on the total average ultrasonic velocity CL in the distance L. That is, only the ultrasonic velocity Cl between the transducers 2, 2' is subjected for the measurement.

As well known, the temperature of a river varies depending on its depth. In summer, the temperature of the surface of a river is high, and it gradually decreases toward the river bed. In winter, on the other hand, the temperature around the surface of the river tends to be higher than the river bottom. Therefore, when merely the substantial surface of a river is subjected to the measurement of the ultrasonic velocity cl, errors in measurements become significantly large since the temperature in a river varies depending on the depth. The length of the distance L measured based on the ultrasonic velocity cl also incurs a large error, and similarly, the measurements in the flow velocity and the flow quantity incur large errors.

In order to show an error incurred in the measurement of the ultrasonic velocity caused by the temperature variation of a river will be described below. Here, a river in summer time is chosen. As illustrated in FIG. 6, the water depth H between the surface and the river bed of the river is equally divided into 3 sections. Suppose, the distribution of the river temperature directly varies in each section.

The river temperature changes 24° C. to 22° C. in the first section which includes the river surface, 22° C. to 18° C. in the second section which is the middle of the river, and 18° C. to 15° C. in the third section which locates at the bottom of the river. To simplify the explanation, the water depth H is supposed to be the same as the distance L, and the vertical distance l is supposed to be 0.2 m. The ultrasonic velocity varies only by the river temperature. The ultrasonic velocity is measured by equation (g) which is a regular relational equation. (Numeral reference T is the average temperature in a section in which an ultrasonic wave propagates.)

When, the water depth H is 3, 4, 5, and 10 m, the local average ultrasonic velocity $c_l$ in the vertical distance l located nearby the river surface is calculated by equation (g). The results are shown in table 1. The total average ultrasonic velocity $C_L$ in the distance L is calculated as 1485.1066 m/s, regardless the water depth. In the prior invention, only the local ultrasonic velocity $c_l$ in the vertical distance l is measured, instead of the total average ultrasonic velocity $C_L$ in the distance L, and the result of the measurement is assumed to be the same as the total average ultrasonic velocity $C_L$. Therefore, the margin of error $\delta_c$ of the total average ultrasonic velocity $C_l$ against $C_L$, which is calculated by equation (h), becomes that as shown in table 1. The margin of error $\delta_L$ included in the distance L, which is calculated by equation (d), and the absolute value ΔL are also shown in table 1.

$$\delta_c = \frac{c_l - c_L}{c_L}, \quad \delta_L = \frac{L' - L}{L} = \frac{\Delta L}{L} \quad (h)$$

TABLE 1

| | | (1 = 0.2 m, $c_L$ = 1485.1055 m/s) | | |
|---|---|---|---|---|
| L( m) | 3 | 4 | 5 | 10 |
| $C_l$ (m/s) | 1495.3979 | 1495.5205 | 1495.5941 | 1495.6431 |
| $\delta_c$ (%) | +0.693 | +0.701 | +0.706 | +0.710 |
| $\delta_L$ (%) | +0.693 | +0.701 | +0.706 | +0.710 |
| Δ L (cm) | +2.08 | +2.80 | +3.53 | +7.10 |

Referring to table 1, in case the depth of the water is 5 m, the margin of error δL, that is the margin of error in the depth H, becomes 0.706% even errors in the time periods t2, t2' and the distance l are supposed to be 0. Although this numeral value does not seem to be large, the absolute value ΔL which is calculated by this value becomes 3.53 cm. In the field of the hydrologic measurement in which the prior invention is performed, the worldwide maximum allowable error is ±1 cm, thus, the error incurred in this prior invention is not acceptable.

The margin of error δV in the flow velocity measurement which is calculated by equation (f) becomes twice larger than that of the ultrasonic velocity error δ c since it is calculated by applying the ultrasonic velocity Cl1 into the equation (f). That is, the margin δV×2×0.706=1.41%. Further, the local flow quantity q is calculated based on the vertical average flow velocity V⊥ and the depth of water H, so that the error in the local flow quantity q incurred caused merely by the measuring method increases to about 2.1% (δL+δV≈2.1%).

In an actual error in the depth measurement δL, the errors in the time periods t2, t2' are added, so that it exceeds 0.706%. Similarly, the error in the flow velocity measurement becomes more than 1.41% as the errors in such as D, Δt are added. As a result, the local flow quantity error exceeds 2.1%. This is the biggest drawback in the prior invention.

In many of the hydrologic measuring posts, there is a measuring method that a local flow velocity and a weight is fixed to a rope, and they are dropped into a river from a bridge through use of a gypsy winch. When the measurement point is as high as 5 to 6 m from the river bed, there is another method in which a flow gauge is fixed to a rod instead of a rope, and the gauge is placed in a river to measure the flow velocity and the flow quantity.

In many measuring posts where no such carriers are equipped, a local flow velocity gauge is carried to measure the flow quantity. However, the prior invention disclosed in Japanese provisional publication No. 9-196727 is difficult to carry because of its size and structure. Further, there is a problem that a carrier is needed in order to carry the apparatus to a measuring point, so that it can only be used in permanent measuring posts.

In hydrologic measuring posts, the water temperature has also been measured as well as the depth and the flow velocity for calculation of the flow quantity. As the environmental problem has been a critical issue in recent years, the measurements of water pollution including the water temperature have widely been performed in especially lakes and reservoirs. Therefore, there is a requirement of providing a measuring apparatus for the water temperature.

Regarding to the measurement of the water temperature, a reversing thermometer has been used, which comprises mercury or alcohol and is read after it is pulled out of the water in each measurement. There is also a thermometer comprising a platinum resistance or a thermistor by which the real-time water temperature can be read on the ground. However, each of the thermometers is only capable of measuring the water temperature at a small point where the sensor of the thermometer takes place. Therefore, it is necessary to measure at many points along the vertical direction in the water, and it required a lot of labor and time for the operation. Besides, they lack the accuracy in measurements.

Further, the sensors used in the conventional thermometers have time constant (delay of response) caused by its principle (in the type comprising mercury and alcohol) or its structure (in the type comprising platinum resistance or thermistor), so that it was necessary to prolong the measuring time period and that it brought measurement errors when the measuring time period was shortened. Besides, it was impossible for the conventional thermometers to perform an accurate measurement where the water temperature varies shortly since they required many measurements at many points and they had the time constant.

Therefore, the object of the present invention is to provide an apparatus that is capable of measuring the depth of water, the flow velocity, the water temperature and the flow quantity of an open channel based on an ultrasonic velocity, and that is used at any place, easy to carry, simple in structure and easy to use.

SUMMARY OF THE INVENTION

According to a first aspect of the invention there is provided an apparatus for measuring the depth of water and the water temperature at any point of an open channel by measuring an ultrasonic propagation time transmitted between a plural number of ultrasonic transducers and by a calculation using an ultrasonic velocity, wherein a slider is attached to a support capable of moving up and down, which is placed in water. A first ultrasonic transducer is fixed to the bottom of the support. A second ultrasonic transducer is positioned above the first ultrasonic transducer. A third ultrasonic transducer is positioned above the second ultrasonic transducer and below the slider. A fourth ultrasonic transducer is fixed to the slider. Each transducer faces with each other.

In this apparatus, when the slider is formed by a float, it is able to move up and down along the support by its buoyant force to take a suitable position. When the support is formed by a flexible material such as a rope and a chain, the support should be provided with a weight at the bottom thereof.

In this structural apparatus, an ultrasonic wave is transmitted and received to measure an ultrasonic propagation time. By this measurement operation, the ultrasonic propagation time periods between the first ultrasonic transducer and the second ultrasonic transducer, and between the third ultrasonic transducer and the fourth ultrasonic transducer are both obtained in numeral value. By substituting the value into an equation for the calculation, the average ultrasonic velocity between the first ultrasonic transducer and the fourth ultrasonic transducer is calculated. And, the distance between the first ultrasonic transducer and the fourth ultrasonic transducer, as well as the water temperature, are also calculated.

In this process, a mere local distance is not subjected to the measurement. In stead, an ultrasonic propagation time period between near the water surface and near the bottom is measured to calculate the ultrasonic velocity. Then, the ultrasonic velocity is averaged. Near the water surface and near the bottom are in many cases contrary in conditions, e.g., the water temperature. Therefore, this averaged ultrasonic velocity is approximately the same as the average ultrasonic velocity of the whole vertical distance of the river depth. As a result of this, the distance (depth) from the first transducer to the fourth transducer and also the water temperature can accurately be measured based on the average ultrasonic velocity.

According to a second aspect of the present invention, there is provided a measuring apparatus, wherein the support is provided with a fifth transducer at the upper stream of the slider and the support, and is also provided with a sixth transducer at the down stream of the slider and the support to measure the ultrasonic propagation time periods between the ultrasonic transducers and ultrasonic velocities to calculate the flow velocity.

This measuring apparatus is characterized in that a first ultrasonic transducer is positioned at the bottom of the support, a second transducer is positioned above the first transducer, a third transducer is positioned above the second transducer and below the slider, and a fourth transducer is positioned at the slider, wherein each transducer faces with each other.

With this apparatus, like the aforementioned case, the average flow velocity in the distance between the first transducer and the fourth transducer is measured. Then, ultrasonic waves are transmitted in two ways between the fifth transducer and the sixth transducer. Using a propagation time difference or measuring a repeated frequency and using the ultrasonic velocity measured in advance, the flow velocity is calculated. In this case, as mentioned before, the ultrasonic velocity is approximately the same as the average ultrasonic velocity of the whole vertical area along the river depth which is the subject of the measurement of the flow velocity. Therefore, the accuracy in measurement of the flow velocity is very high.

According to a third aspect of the present invention, there is provided a flow velocity measuring apparatus, wherein a level bar is fixed either to a slider which is attached to a support capable of moving up and down or the bottom of the support. The level bar is provided with a fifth transducer at one end and with a sixth transducer at the other end, each of which faces with each other. The ultrasonic propagation time difference between the fifth and sixth transducers and a repeated frequency are measured and operated with the apparatus.

Like the first and second aspects of the present invention, a first, second, third and fourth ultrasonic transducers are positioned in a face-to-face manner. And, the average ultrasonic velocities in the distances from the first to the fourth transducers are measured.

In the third aspect of the present invention, the first or the fourth transducer can be used as the sixth transducer.

In the second, third and fourth aspects of the present invention, it is desirable that the slider is constituted with a float, and that the bottom of the support is constituted with a weight.

DETAILED DESCRIPTION OF THE INVENTION

Figure 1:
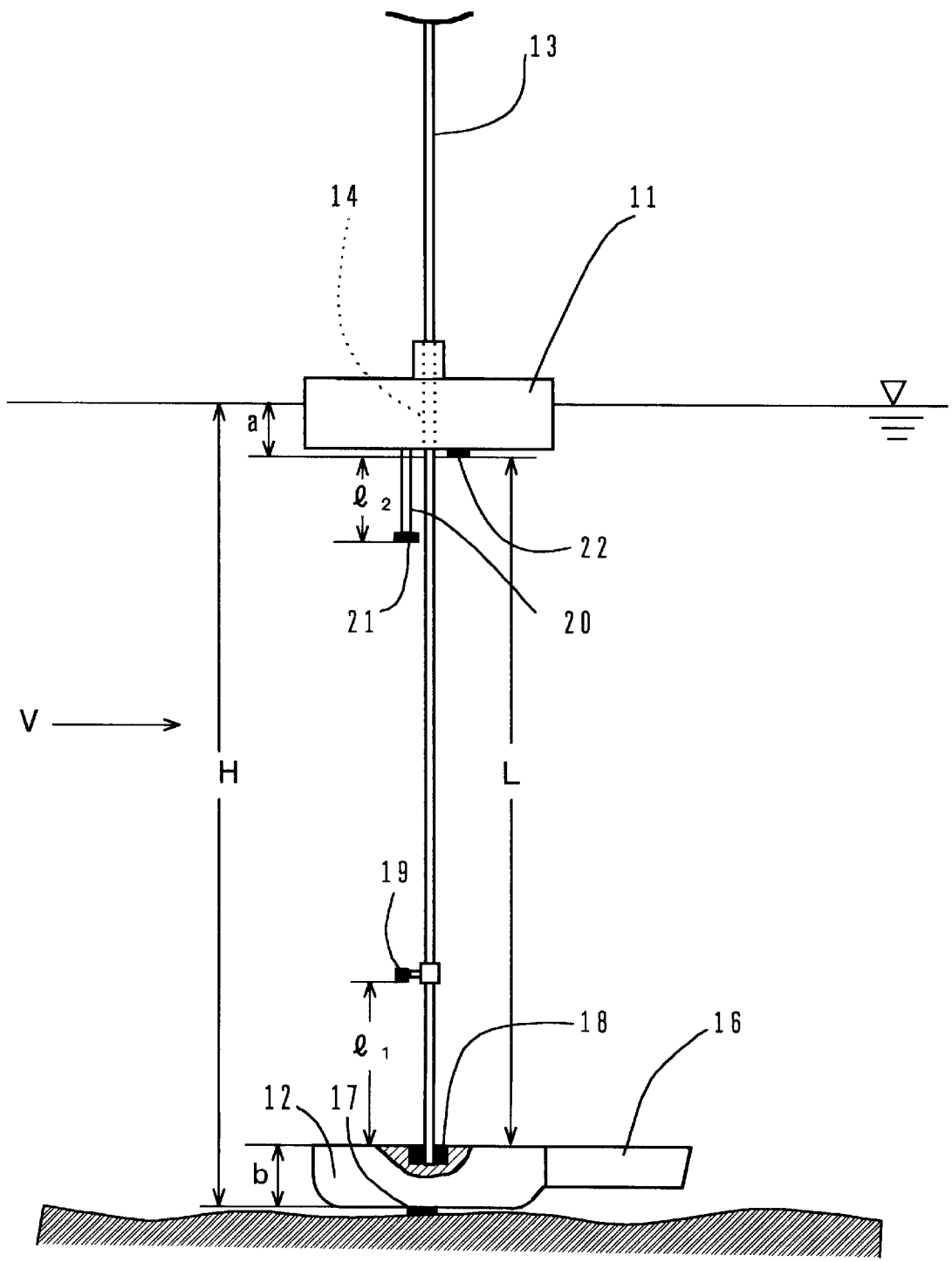
FIG. 1 is an explanatory drawing that illustrates a principle of the apparatus for measuring the depth of water and the water temperature of an open channel according to the present invention.

First, the basic structure of an apparatus for measuring the water depth and the water temperature according to the present invention will be described below. As illustrated in FIG. 1, a support 13 placed in the water is provided with a slider 11 capable of moving up and down and of taking a position on the water surface. The support 13 is also provided with a first ultrasonic transducer 18 at the bottom thereof and a second transducer 19 at a distance 11 away from the first transducer 18.

A small bar 20 is attached to the under surface of the slider 11 capable of removing. The small bar 20 is provided with a third ultrasonic transducer 21. The slider 11 is provided with a fourth ultrasonic transducer 22 at the under surface thereof. There is provided a distance 12 between the third transducer 21 and the fourth transducer 22.

Therefore, the second transducer 19 takes a position above the first transducer 18, and the third transducer 21 takes a position above the second transducer 19 and below the slider 11, and the fourth transducer 22 takes a position under surface of the slider 11. Each transducer faces with each other.

There is a distance a between the fourth transducer 22 and the water surface since the slider 11 takes a position on the water surface. There is a distance b between the upper surface of the first transducer 18 and the river bed. Supposing, the distance between the fourth transducer 22 and the first transducer 18 is the distance L, the water depth H=L+(a+b).

In the above mentioned structure, in order to measure the water depth or the water temperature at a measuring position, the ultrasonic propagation time period is measured at first. That is, when the first transducer 18 is used as an ultrasonic transmitter and it transmits an ultrasonic wave, this ultrasonic wave is received by the second transducer 19, the third transducer 21 and the fourth transducer 22 in this sequence. Instead of this, it is possible that the fourth transducer 22 is used as a transmitter, and that the third transducer 21, second transducer 19 and the first transducer 18 may receive the ultrasonic wave in this sequence.

Further, the second transducer 19 or the third transducer 21 may be used as a transmitter, and the other three transducers may be used as receivers. In sum, one or more transducer(s) is/are used to transmit ultrasonic wave(s), and the rest of the transducer(s), at least one, is/are used to receive the ultrasonic wave(s).

Figure 4:
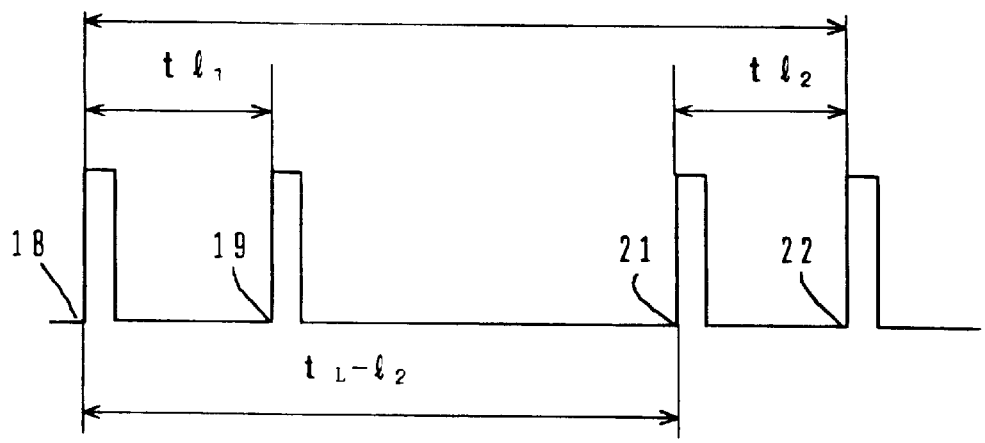
FIG. 4 is a time chart showing an ultrasonic propagation time period.
Figure 5:
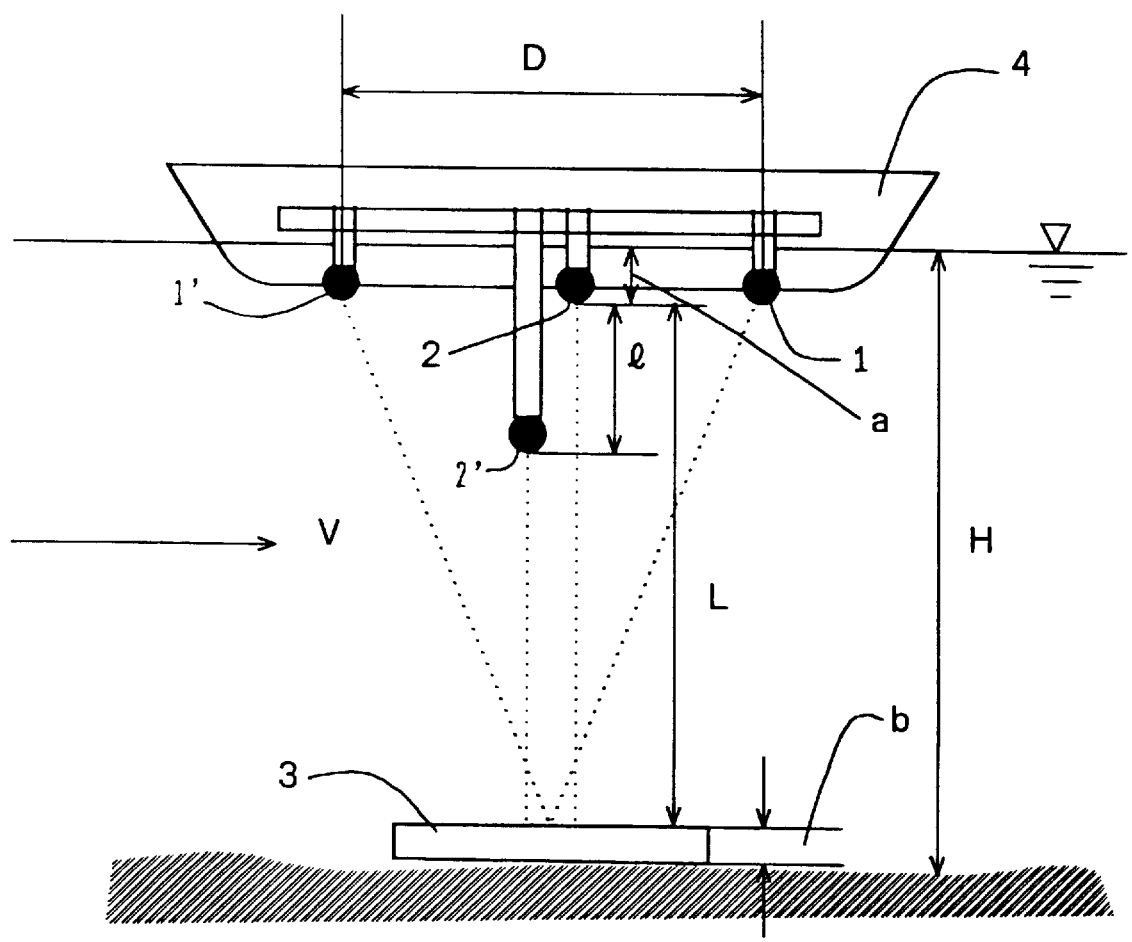
FIG. 5 is a explanatory drawing of an example of a prior art.

For example, FIG. 4 illustrates a timing chart in a rectangular form of an ultrasonic wave transmitted from the first transducer. This illustration shows, from the left to the right, the transmit timing of the first transducer 18, the receiving timings of the second transducer 19, the third transducer 21 and the fourth transducer 22.

Suppose, the propagation time period between the first transducer 18 and the fourth transducer 22 is tL, the propagation time period between the first transducer 18 and the second transducer 19 is tl1, the propagation time period between the third transducer 21 and the fourth transducer 22 is tl2, and the propagation time period between the first transducer 18 and the third transducer 21 is tL–l2, then tl2=tL–tL–l2.

By using the propagation time periods tL, tl1 and tl2, an ultrasonic velocity c is calculated by equation (1), and the length of the distance L is calculated by equation (2).

$$c = \frac{1}{2}(c_{l_1} + c_{l_2}) = \frac{1}{2}\left(\frac{l_1}{t_{l_1}} + \frac{l_2}{t_{l_2}}\right) \tag{1}$$

$$L = c \cdot t_L = \frac{t_L}{2}\left(\frac{l_1}{t_{l_1}} + \frac{l_2}{t_{l_2}}\right) \quad (2)$$

The ultrasonic velocity C of the distance L is calculated by the equation (1), and the length of the distance L is calculated by the equation (2). Therefore, the depth of the water is calculated by the aforementioned equation, that is the water depth H=L+(a+b).

Here, the ultrasonic velocity C is measured near the water surface and near the river bed, and the average ultrasonic velocity is calculated based on them to counterbalance the differences. Since the conditions such as the water temperature contradicts utmost between near the water surface and near the river bed, an error in the average ultrasonic velocity C becomes minimum. Thus, the average ultrasonic velocity C corresponds to the total average ultrasonic velocity $C_L$ in the distance L without being influenced by the water temperature which varies depending on the depth in a regular water temperature range.

Figure 6:
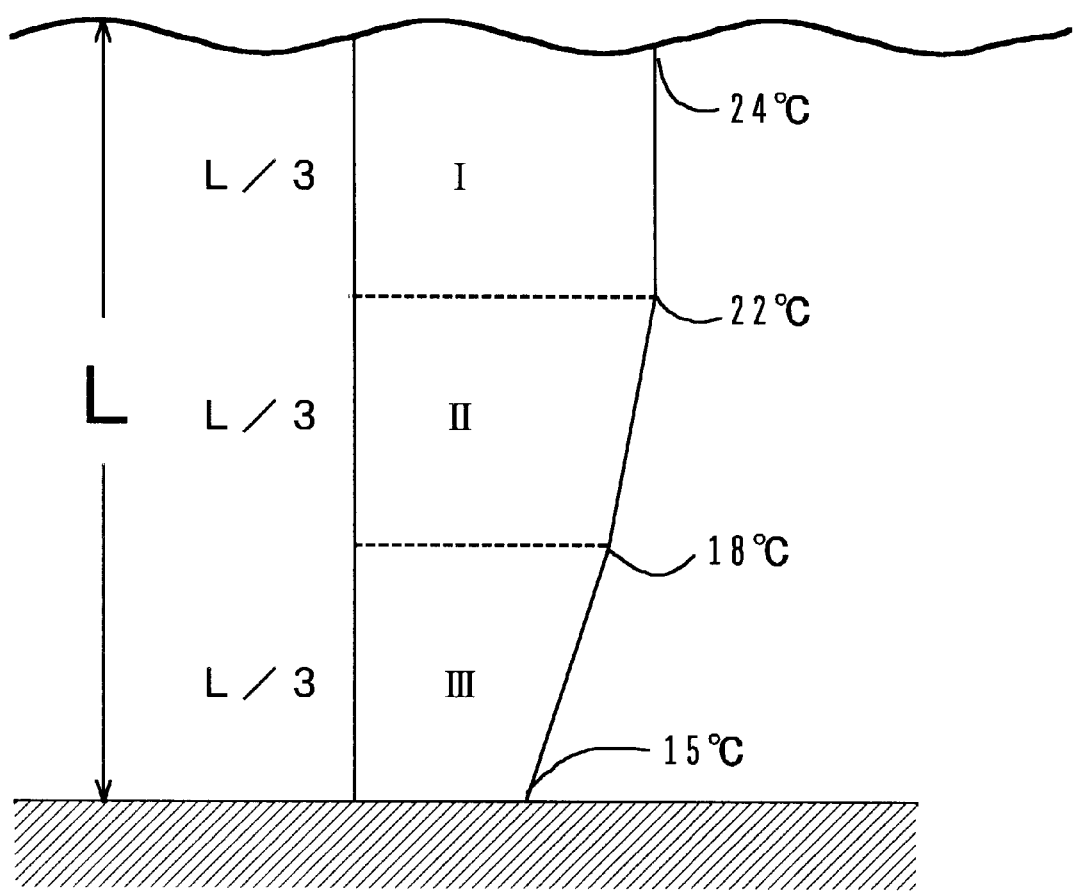
FIG. 6 is a cross section explanatory drawing that shows the temperature distribution between the water surface of a river and the river bed thereof.

According to the present invention, a measurement error caused by a condition regarding to the water temperature is minimal. This will be demonstrated below using numeral values. To compare the present invention to the prior invention, the temperature distribution as illustrated in FIG. 6 is again used. Under the condition that $l_1=l_2=0.2$ m, the ultrasonic velocities $C_L$, $C_{l1}$ and $C_{l2}$ are calculated by the equation (g). The margins of ultrasonic velocity measurement errors $\delta c$, $\delta c_1$, $\delta c_2$ are calculated by the equation (3). Further, the margin of the water depth measurement error $\delta L$, $\Delta L$ are calculated respectively. Table 2 shows the results in respect to each water depth.

$$\delta_c = \frac{c - c_L}{c_L}, \quad \delta_{c_1} = \frac{c_{l_1} - c_L}{c_L}, \quad \delta_{c_2} = \frac{c_{l_2} - c_L}{c_L} \quad (3)$$

TABLE 2

| L(m) | ($l_1 = l_2 = 0.2$ m, $C_L = 1485.1055$ m/s) | | | |
|---|---|---|---|---|
| | 3 | 4 | 5 | 10 |
| $C_{l1}$ (m/s) | 1472.7705 | 1472.5550 | 1472.4257 | 1472.1667 |
| $\delta C_1$ (%) | −0.831 | −0.845 | −0.854 | −0.871 |
| $C_{l2}$ (m/s) | 1495.3979 | 1495.5205 | 1495.5941 | 1495.6431 |
| $\delta C_2$ (%) | +0.693 | +0.701 | +0.706 | +0.710 |
| C (m/s) | 1484.0842 | 1484.0378 | 1484.0099 | 1483.9049 |
| $\delta C$ (%) | −0.0688 | −0.0719 | −0.0738 | −0.0808 |
| $\delta_L$ (%) | −0.0688 | −0.0719 | −0.0738 | −0.0808 |
| $\Delta L$ (cm) | −0.206 | −0.288 | −0.369 | −0.808 |

Comparing the data in table 2 with that in table 1, both measurements and calculations are completed under the same conditions, so that $C_L=1485.1055$ m/s in both cases. $C_{l1}$ and $C_{l2}$ indicate the local average ultrasonic velocities in the distance $l_1$ and $l_2$ respectively as shown in FIG. 1. $C_{l2}$ corresponds to the local average ultrasonic velocity $C_l$ in the vertical distance l near the water surface in the previous invention since $C_{l2}=0.2$ m=l.

According to the present invention, as clearly understood by comparison of both tables, the margin of error $\delta c$ of the ultrasonic velocity C, which is calculated by the equation (1), decreases to 1/10 of that of the prior invention at any water depth. The reason of the eminent decrease in the margin of the ultrasonic velocity error $\delta c$ is that, as shown in table 2, the margins of the ultrasonic velocity errors $\delta c_1$, $\delta c_2$ in the distances $l_1$, $l_2$ are negative and positive respectively and that the ultrasonic velocity C is calculated by the equation (1). This counterbalances each margin of error.

In case the water depth is 5 m, the margin of error $\delta c$ in the present invention is only 0.0738% while the margin of error $\delta c$ in the prior invention is 0.706%. As a result of this, the margin of the water depth measurement error $\delta L$ decreases to 1/10, so that the absolute value $\Delta L$ is only 0.37 cm. When the water depth is even 10 m, the absolute value $\Delta L$ is still 0.8 cm. This fully satisfies the error allowance required in the hydrologic measurement. Further, as will be described below, the margin of flow velocity measurement error decreases to 0.15% from 1.41%, and that of the flow quantity measurement error decreases to 0.22% from 2.1%. Both decrease 1/10 compared to the prior invention.

In this preferred embodiment of the present invention, as described above, the second ultrasonic transducer 19 fixed to the support 13 is capable of moving up and down, so that the distance 11 can be adjusted. The small bar 20 can be replaced by another bar of different length, so that the distance l2 is also adjusted.

As the distances $l_1$, $l_2$ are arranged to be longer, the accuracy in a measurement of the ultrasonic velocity, the water depth and the water temperature increases. It is desirable that $l_1=l_2=L/3$. When a measurement operation is performed in a deep lake or a reservoir using such as a boat, the distance l may be arranged longer in length as opposed to the section L in order to improve the accuracy in measurement since the flow velocities of the lake and the reservoir are minimal. Contrary to this, when the depth of water is shallow, the distance l should be arranged shorter in length. In case, as will be described below, that the support 13 is constituted with a flexible material such as a rope and that the rope does not keep a complete vertical position as it is carried by the water flow, the error in measurement of the water depth will be prevented if the distances $l_1$, $l_2$ are adjusted shorter in length. It is because the rope corresponding to the distance $l_1$, $l_2$ can be kept subvertical as the distances 11, 12 are short.

As a method of measuring the ultrasonic propagation time period in a distance, it is not limited to use four transducers. It is possible to exclude either or both of the first transducer 18 and the fourth transducer 22. In this case, the measurement operation is completed using the second transducer 19 and the third transducer 21 with a combination of either the first transducer 18 or the fourth transducer 22.

Then, in order to obtain the propagation time in a certain distance, the time period between the time an ultrasonic wave is transmitted from either one of the transducers and the time it is directly received by another transducer, and the time it returns to the same transducer after reflecting by a bottom unit 12, river bed, a slider 11 or the water surface is measured. However, such operation requires a lot of work; a number of transmitting operations is needed in each measurement; it requires to provide a transducer capable of both transmitting and receiving ultrasonic waves; a control software, a calculation software, a switching circuit and the like become complicated. Further, when the water is deep, the distances 11, 12 should be arranged longer in length, therefore, there may be a case that the ultrasonic wave does not reach to the transducer as it should be since it damps by reflection.

As a forming material of a support 13, a straight bar is supposed to be used. The support 13 may be formed by a bar (a rod) which has been used among approximately the all people working for flow quantity measurement operations using a propeller-type local flow velocity. Further, a flexible material such as a rope and a chain may be used as a forming material of the support 13. When the flexible material is used, it is desirable to connect a bottom unit 12 to the bottom of the support 13 as a weight to prevent the flexible material from bending caused by the water flow. (That is, the flexible material can be kept in a vertically standing posture.)

A slider 11 is equipped to the support 13 capable of moving up and down, and it is fixed thereto by a connector at the water surface while the support 13 stands vertically in the water. By forming a slider 11 with a float, the slider 11 is able to float on the water surface in any water depth and water level, so that a labor for positioning the slider 11 at a right position can be saved.

An attachment of the float-type slider 11 to the support 13 is completed by, for example, making an opening 14 at the middle of the slider 11, and inserting the support 13 formed by a bar or a rope into the opening 14, engaging the slider 11 with the support 13 capable of sliding up and down. However, the attachment is not limited to this: the slider 11 may be provided with a ring (not shown) at a part thereof, and the support 13 may be put through the ring.

When the support 13 is formed by a bar, by positioning the support 13 in an upright posture in the water, the slider 11 can be held right above the bottom unit 12 even the support 13 is pushed by the water flow. And, when the support 13 is formed by a flexible material such as a rope, the slider 11 can be held above the bottom unit 12 by straining the support 13 above the bottom unit 12. In case the slider 11 is formed by a float, it automatically moves up and down following the water level. However, such slider 11 may rotates around its axis, the opening 14, as it receives the water flow.

Figure 2:
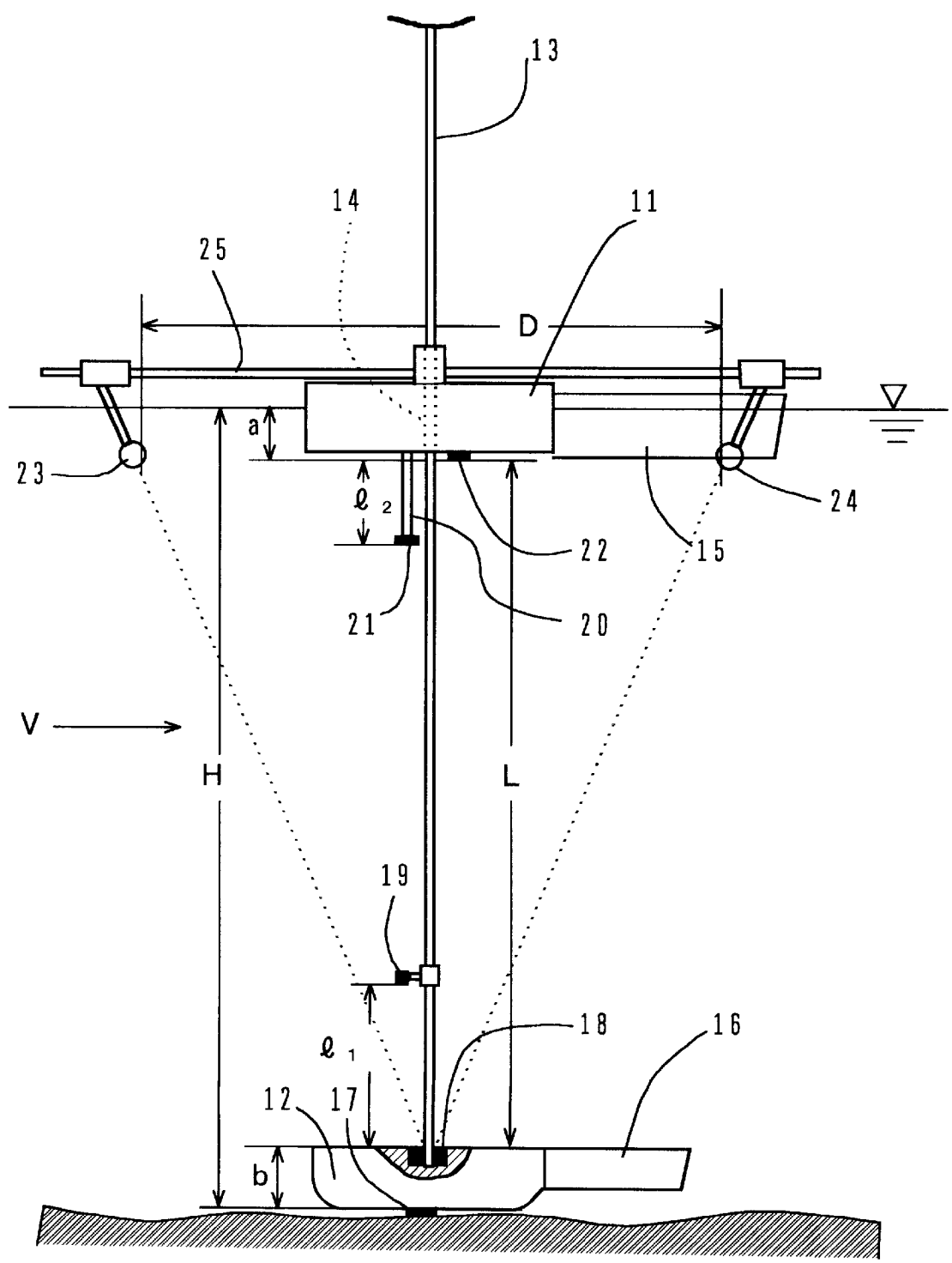
FIG. 2 is an explanatory drawing that explains an apparatus for measuring the flow velocity of an open channel according to the present invention.

Therefore, it is desirable to form the slider 11 into a streamlined shape and to provide a rudder 15 at the edge thereof in order to make the slider 11 to firmly face toward a certain direction corresponding to the water flow (see FIG. 2). By comprising the rudder 15, it is possible to correspond the axial direction of the streamline-shaped slider 11 in the direction of the water flow. Further, in case the support 13 is formed by a bar, either the support 13 or the slider 11 may be comprised of a concave portion and the other may be comprised of a convex portion, engaging the concave and the convex portions to connect the support 13 with the slider 11 (not shown in drawings).

The same rotational problem may arise in a bottom unit 12 when it is moving down in the water when a support 13 is formed, for example, of a rope, so that it is desirable to provide a rudder 16 to the bottom unit 12. By doing so, the rope is prevented from screwing caused by a pivotal action of the bottom unit 12. At the same time, the bottom unit 12 can approximately be placed on the river bed forwarding to the certain direction in each operation. The bottom unit 12 is provided with a contact sensor 17 to confirm the contact with the river bed.

In case the support 13 is put through the opening 14 of the slider 11, the opening 14 is preferably provided with, for example, a polyurethane-made cylinder having a small coefficient of friction in order for the float-type slider 11 to move up and down smoothly and to turn smoothly (not shown in drawings).

There is provided a first ultrasonic transducer 18 on the center of the bottom unit 12 which is fixed to the bottom of the support 13. It is desirable that each transducer takes a position on a circle around the support 13 to prevent deterioration of the propagation efficiency caused by a positional relationship in which a transducer takes a position behind another transducer. In such a case, it is preferable that the first transducer 18 is formed into a doughnut shape which oscillates in the axial directions in order to ensure the other transducers to directly receive the ultrasonic wave the first transducer 18 has transmitted.

Especially, when the support 13 is formed by a bar, it is desirable to provide a level gauge at the top edge of the support 13 to keep it in a vertical posture. It is also desirable to provide a flange at the bottom edge of the bottom unit 12 to prevent the bottom edge portion of the support 13 from plunging into the river bed, and to protect the first transducer 18 from any damage (both are not shown in drawings).

When the float-type slider 11, which floats on the water surface, is used, there is a distance a between the fourth transducer 22 and the water surface. Also, when the bottom unit 12 is used and the first transducer 18 is fixed thereto, there is created the distance b between the first transducer 18 and the river bed since the bottom unit 12 has a thickness.

As described previously, the water temperature and the ultrasonic velocity are expressed by the relational equation (g). Thus, the ultrasonic velocity C is calculated by the equation (g). By using the apparatus according to the present invention and equation (4) which is an arranged formula of the equation (g), the highly accurate average ultrasonic velocity C can be obtained. Therefore, the water temperature T at the point the ultrasonic velocity C is measured can also be calculated with the same apparatus and the equation (4). As a result of this, a measurement of the water temperature which is needed for the hydrologic and water pollution measurements can accurately be performed.

$$T = 74 - \sqrt{63694.27 - \frac{c}{0.0244}} \tag{4}$$

Besides the aforementioned apparatus for measuring the water depth and the water temperature, an apparatus for measuring the flow velocity of an open channel such as a river is formed by further comprising a fifth transducer 23 and a sixth transducer 24 for transmitting and receiving ultrasonic waves and by measuring a propagation time difference or a repeated frequency.

Referring to FIG. 2, a streamline-shaped slider 11 is provided with a level bar 25 along its length direction capable of removing. At the both sides of the level bar 25, there are provided a fifth transducer 23 at one side and a sixth transducer 24 at the other side, making a distance D in between them and each taking a position at the equal distance from the center of the slider 11.

Although the distance D should be arranged longer in length in order to increase accuracy in measurement, the distance is determined depending on conditions such as the depth of the water. The fifth transducer 23 and the sixth transducer 24 are attached to the level bar 25 capable of sliding or rotating for adjustment of angles. The fifth and sixth transducers 23, 24 are arranged to take positions just below the water surface.

In the preferred embodiment according to the present invention as illustrated in FIG. 2, the fifth transducer 23 is positioned just below the water surface in the upstream of the slider 11, and the sixth transducer 24 is positioned just below the water surface in the downstream of the slider 11. An ultrasonic wave transmitted from the fifth transducer 23 runs toward the river bed and it reaches to the river bed, a bottom unit 12 or the surface of the first transducer 18 fixed to the bottom unit 12, then it reaches to the sixth transducer 24 after reflecting by either one of them. The time period t56 between the time the ultrasonic wave is transmitted from the fifth transducer 23 and the time it is received by the sixth transducer 24 is measured. Also, the time period t65 between the time an ultrasonic wave is transmitted from the sixth transducer 24 and the time it reaches to the fifth transducer 23 after reflecting at the river bed, the bottom unit 12 or the first transducer 18 is measured. Then, the vertical average flow velocity $V\perp$ in the distance L is calculated by equation (5) which is similar to the equation (e).

$$V_\perp = \frac{t_{65} - t_{56}}{2D} c^2 \qquad (5)$$

$$V_\perp = \frac{\Delta t}{2D} c^2 = \frac{\Delta t}{8D} \left( \frac{l_1}{t_{l_1}} + \frac{l_2}{t_{l_2}} \right)^2 \qquad (6)$$

By substituting the equation (1), by which the ultrasonic velocity C is obtained, into the equation (5), equation (6) is obtained. By the equation (6), the concrete vertical average flow velocity $V\perp$ is calculated. Further, by using the equation (2) and the formula of the water depth H=L+(a+b), a local cross section is obtained. By multiplying the vertical averaged flow velocity $V\perp$ by the local cross section, the local flow quantity in each divided section is obtained. By adding all the local flow quantities, the total flow quantity of the open channel is obtained.

Further, by applying a software in a controller (not shown in drawings) while inputting the widths B of the divided sections, the water depth, the flow velocity and the flow quantity are automatically and easily measured at once.

In the preferred embodiment as illustrated in FIG. 2, it shows a structure that the level bar 25 is attached to the slider 11, but the level bar 25 may be attached to the bottom of the support 13 or the bottom unit 12 instead, and the fifth transducer 23 and the sixth transducer 24 may be positioned near the river bed. In such a case, it is arranged that an ultrasonic wave transmitted between the fifth transducer 23 and the sixth transducer 24 reflects by the water surface or the under surface of the slider 11. In each of the preferred embodiments according to the present invention, the level bar 25 is structured capable of removing. It is because the level bar 25 is unneeded when the apparatus is used for measuring the water depth and the water temperature only.

When the river bed has a big concave-convex surface, it is preferable that the level bar 25 is attached to the slider 11 in order for an accurate measurement. By adopting such structure, it is easy to adjust a distance between the fifth transducer 23 and the sixth transducer 24, and is also easy to adjust angles of the fifth and the sixth transducers 23, 24 toward the bottom of the support 13.

Normally, the flow velocity is fast and the flow pressure is high near the water surface, so that in the structure as illustrated in FIG. 2, the level bar 25 including the slider 11 become unstable. In case the slider 11 is formed by a float, it must be made large to obtain a big buoyant force. Such problem is solved when the level bar 25 is fixed to the bottom of the support 13 or to the bottom unit 12.

Figure 3:
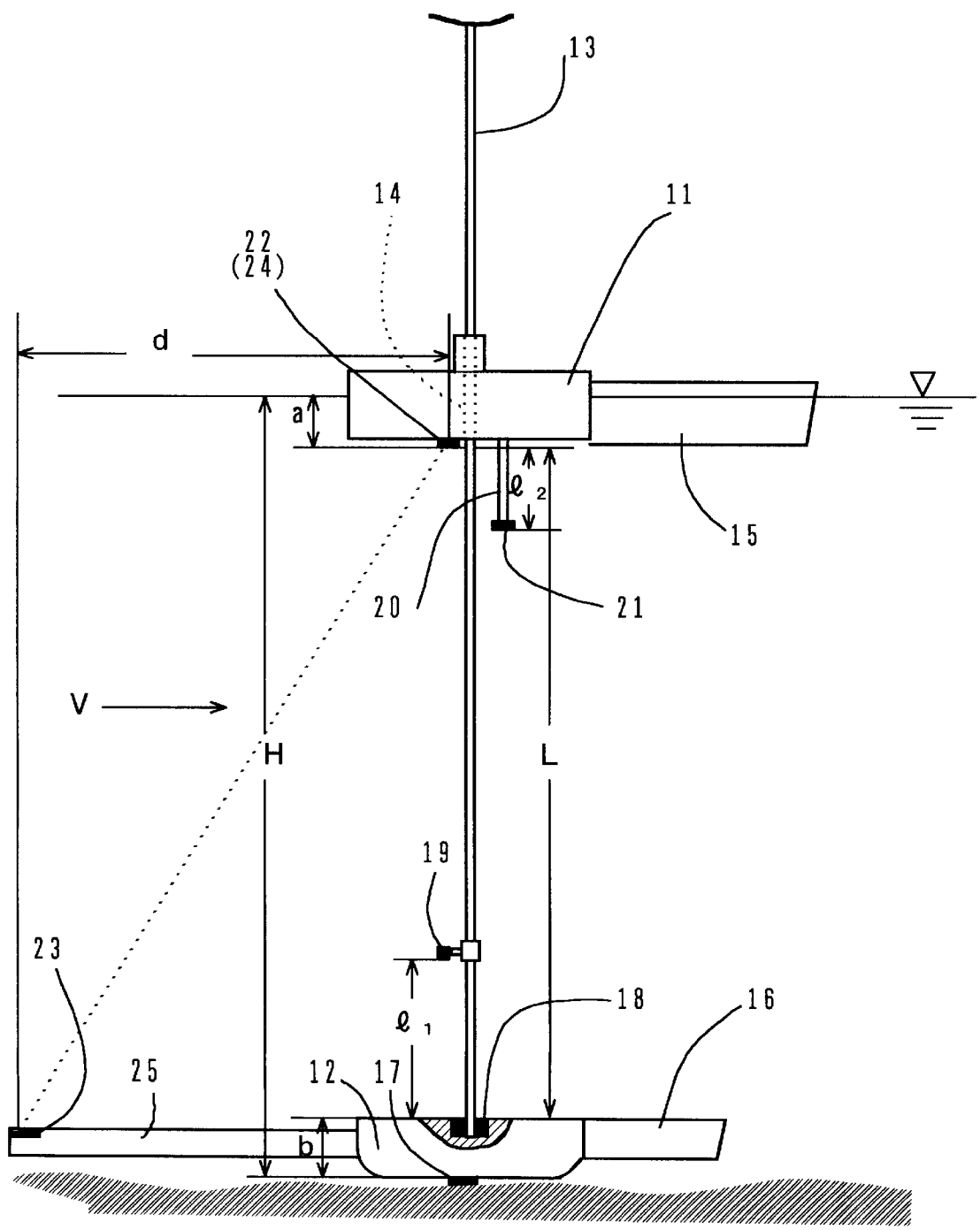
FIG. 3 is an explanatory drawing that explains an apparatus for measuring the depth of water, the water temperature and the flow quantity of an open channel according to the present invention.

As an apparatus for measuring the flow velocity after measuring an ultrasonic propagation time period and a repeated frequency, there is provided another apparatus which is illustrated in FIG. 3. In this structural apparatus, a level bar 25 having a fifth transducer 23 at the edge thereof is fixed to either a slider 11 or the bottom of a support 13 or a bottom unit 12. A sixth transducer 24 for transmitting and receiving ultrasonic waves is fixed to either the slider 11 or the bottom of the support or the bottom unit 12 facing the fifth transducer 23. The fifth transducer 23 and the sixth transducer 24 face with each other.

In this embodiment, when the level bar 25 is attached to the bottom of the support 13 or the bottom unit 12, the sixth transducer 24 may be substituted by a fourth transducer 22 which is attached to the under surface of the slider 11. Further, when the level bar 25 is attached to the slider 11, the sixth transducer 24 may be substituted by a first transducer 18 which is attached to the upper surface of the bottom unit 12.

According to this embodiment, the propagation time period t56 between the time an ultrasonic wave is transmitted from the fifth transducer 23 and the time it reaches to the sixth transducer 24 is measured. Also, the propagation time period t65 between the time an ultrasonic wave is transmitted from the sixth transducer 24 and it is received by the fifth transducer 23 is measured. Then, the vertical average flow velocity $V\perp$ is calculated by equation (7).

$$V_\perp = \frac{t_{65} - t_{56}}{2d} c^2 = \frac{\Delta t}{8d} \left( \frac{l_1}{t_{l_1}} + \frac{l_2}{t_{l_2}} \right)^2 \qquad (7)$$

The method for obtaining the ultrasonic velocity and the accuracy thereof according to the apparatuses shown in FIGS. 2 and 3 are the same as that shown in FIG. 1. And, the methods for obtaining the water depth and the water temperature are also the same in all the embodiments.

According to the present invention, a plural pairs of transducers are used. They are the first, second, third and fourth transducer 18, 19, 21, 22 and the fifth and sixth transducers 23, 24. In any one of the pairs, only an ultrasonic propagation time period between the pair is measured and nothing else is subjected to the measurement, and each measurement completes at once. Therefore, a measurement operation in each pair can be completed one by one. (When, all the measurement operations in all pairs are performed at once, noise will arise.) According to the present invention, it is only needed a mechanism (circuit) in an apparatus which is capable of transmitting an ultrasonic wave and of measuring its propagation time period. Besides this, merely an automatic transfer switch is needed. Therefore, an apparatus according to the present invention is very simple in structure and operation and is light.

In the aforementioned embodiments according to the present invention, a certain type of structure is consistently described, in which the first transducer 18 is positioned on or near the river bed, the fourth transducer 22 is positioned on or near the water surface, the second transducer 19 and the third transducer 21 are positioned in between the first and the fourth transducers 18, 22, in order to measure the average ultrasonic velocity, the average water temperature and the water depth between the river bed and the water surface. The embodiments also comprise the fifth transducer 23 and the sixth transducer 24 positioned just below the water surface or near the river bed.

However, each transducer's position is not limited to such position as described. For example, it is not nil that the accurate water temperature and the water depth between the middle point and the river bed or between the middle point and the water surface must be measured, based on the middle point in between the water surface and the river bed. In such a case, it is supposable that the first ultrasonic transducer 18 is positioned at the river bed while the fourth transducer 22 is positioned at the middle point, or the first transducer 18 is positioned at the middle point while the fourth transducer 22 is positioned just below the water surface.

Similarly, there may be a case that merely the middle section is subjected to the measurement of the flow velocity, or merely above or below the middle section is subjected to the measurement in, for example, hydraulics study and the like.

An apparatus according to the present invention is able to measure the average ultrasonic velocity in a distance, which is very similar to the average ultrasonic velocity of the whole distance of an open channel. Therefore, based on this, an accurate measurement of the water depth can be performed.

Also, with the apparatus, the average flow velocity and the water temperature between the water surface and the river bed can accurately be measured at once, since the measurement is achieved based on the accurately measured ultrasonic velocity.

Further, an apparatus according to the present invention is easy to carry, so that a carrier conventionally needed for installing the parts of an apparatus is unneeded. The apparatus is also highly useful since it is able to utilize an ordinary bar and a rope as it is, which is used in a conventional flow gauge, e. g., a propeller type gauge.

What is claimed is:

1. An apparatus for measuring the depth of water or the water temperature at any point of an open channel by measuring an ultrasonic propagation time transmitted between a plural number of ultrasonic transducers and by a calculation using an ultrasonic velocity to obtain an accurate average ultrasonic velocity in a vertical direction, wherein a slider is attached to a support capable of moving up and down, said support being place in water, a first ultrasonic transducer is fixed to the bottom of the support, a second ultrasonic transducer is positioned above the first ultrasonic transducer, a third ultrasonic transducer is positioned above the second ultrasonic transducer and below the slider, and, a fourth ultrasonic transducer is fixed to the slider, each transducer faces with each other.

2. An apparatus for measuring the water depth, the water temperature or the flow velocity claimed in claim 1, wherein the slider is formed by a float.

3. An apparatus for measuring the water depth, the water temperature or the flow velocity claimed in claim 2, wherein the bottom of the support is formed by a weight.

4. An apparatus for measuring the water depth, the water temperature or the flow velocity claimed in claim 1, wherein the bottom of the support is formed by a weight.

5. An apparatus for measuring the flow velocity at any point in water by measuring an ultrasonic propagation time transmitted between a plural number of ultrasonic transducers and by a calculation using an ultrasonic velocity, to obtain an accurate average ultrasonic velocity in a vertical direction, comprising a fifth transducer which is positioned at the upstream of a slider attached to a support capable of moving up and down, or at the upstream of the bottom of the support for tansmitting and receiving an ultrasonic wave, a sixth transducer is positioned at the down stream of the slider or at the down stream of the bottom of the support for transmitting and receiving an ultrasonic wave, wherein, a first ultrasonic transducer is fixed to the bottom of the support, a second ultrasonic transducer is positioned above the first ultrasonic transducer, a third ultrasonic transducer is positioned above the second ultrasonic transducer and below the slider, and, a fourth ultrasonic transducer is fixed to the slider, each transducer faces with each other.

6. An apparatus for measuring the water depth, the water temperature or the flow velocity claimed in claim 5, wherein the slider is formed by a float.

7. An apparatus for measuring the water depth, the water temperature or the flow velocity claimed in claim 5, wherein the bottom of the support is formed by a weight.

8. An apparatus for measuring the flow velocity at any point in water by measuring an ultrasonic propagation time transmitted between a plural number of ultrasonic transducers and by a calculation using an ultrasonic velocity, to obtain an accurate average ultrasonic velocity in a vertical direction, comprising a fifth transducer which is fixed to the edge of a level bar, the level bar is fixed either to a slider or the bottom of the support, the slider is attached to the support capable of moving up and down, a sixth transducer is fixed to the slider, the bottom of the support or a place nearby the bottom of the support, facing the fifth transducer, wherein a first ultrasonic transducer is fixed to the bottom of the support, a second ultrasonic transducer is positioned above the first ultrasonic transducer, a third ultrasonic transducer is positioned above the second ultrasonic transducer and below the slider, and, a fourth ultrasonic transducer is fixed to the slider, each transducer faces with each other.

9. An apparatus for measuring the flow velocity claimed in claim 8, wherein the sixth transducer is substituted by either the first transducer or the fourth transducer.

10. An apparatus for measuring the water depth, the water temperature or the flow velocity claimed in claim 9, wherein the slider is formed by a float.

11. An apparatus for measuring the water depth, the water temperature or the flow velocity claimed in claim 9, wherein the bottom of the support is formed by a weight.

12. An apparatus for measuring the water depth, the water temperature or the flow velocity claimed in claim 8, wherein the slider is formed by a float.

13. An apparatus for measuring the water depth, the water temperature or the flow velocity claimed in claim 8, wherein the bottom of the support is formed by a weight.

* * * * *